(12) United States Patent
Hwang et al.

(10) Patent No.: US 9,726,638 B2
(45) Date of Patent: Aug. 8, 2017

(54) APPARATUS FOR IN REAL TIME DETECTING BIOLOGICAL PARTICLE AND NON-BIOLOGICAL PARTICLE IN THE ATMOSPHERE AND METHOD FOR DETECTING BIOLOGICAL PARTICLE AND NON-BIOLOGICAL PARTICLE USING THE SAME

(71) Applicant: INDUSTRY-ACADEMIC COOPERATION FOUNDATION YONSEI UNIVERSITY, Seoul (KR)

(72) Inventors: Jungho Hwang, Seoul (KR); Sang Gu Lee, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/714,453

(22) Filed: May 18, 2015

(65) Prior Publication Data
US 2015/0330945 A1   Nov. 19, 2015

(30) Foreign Application Priority Data
May 16, 2014   (KR) .......................... 10-2014-0059277

(51) Int. Cl.
*G01N 27/68* (2006.01)
*B03C 3/38* (2006.01)
(Continued)

(52) U.S. Cl.
CPC ............. *G01N 27/68* (2013.01); *B03C 3/017* (2013.01); *B03C 3/06* (2013.01); *B03C 3/12* (2013.01);
(Continued)

(58) Field of Classification Search
None
See application file for complete search history.

(56) References Cited

U.S. PATENT DOCUMENTS

| 5,154,733 A * | 10/1992 | Fujii | ....................... B03C 3/383 |
| | | | 209/129 |
| 5,254,861 A * | 10/1993 | Carpenter | .............. G01N 27/66 |
| | | | 250/379 |

(Continued)

FOREIGN PATENT DOCUMENTS

| KR | 10-2006-0056576 A | 5/2006 |
| KR | 10-0710692 B1 | 4/2007 |

(Continued)

*Primary Examiner* — Jermele M Hollington
*Assistant Examiner* — Suresh K Rajaputra
(74) *Attorney, Agent, or Firm* — LRK Patent Law Firm

(57) ABSTRACT

The present invention relates to apparatus for in real time detecting biological particles and non-biological particles in the atmosphere, the apparatus comprising: an impactor adapted to sort the biological particles and non-biological particles absorbed from the outside by size; a charger adapted to charge the biological particles and non-biological particles sorted by means of the impactor to specific charge (positive or negative charge); a separator adapted to introduce the biological particles and non-biological particles charged by the charger thereinto and to sort the biological particles and non-biological particles charged to different charge quantities from each other; and a particle measurement sensor adapted to measure the concentrations of the particles discharged from an outlet.

13 Claims, 11 Drawing Sheets

(51) Int. Cl.
  *G01N 15/06*    (2006.01)
  *G01N 1/22*     (2006.01)
  *B03C 3/017*    (2006.01)
  *B03C 3/06*     (2006.01)
  *B03C 3/12*     (2006.01)
  *B03C 3/36*     (2006.01)
  *B03C 3/41*     (2006.01)
  *B03C 3/47*     (2006.01)
  *G01N 15/00*    (2006.01)
  *G01N 15/02*    (2006.01)

(52) U.S. Cl.
  CPC .............. *B03C 3/365* (2013.01); *B03C 3/38* (2013.01); *B03C 3/41* (2013.01); *B03C 3/47* (2013.01); *G01N 1/2208* (2013.01); *G01N 1/2273* (2013.01); *G01N 15/0656* (2013.01); *B03C 2201/06* (2013.01); *G01N 15/0255* (2013.01); *G01N 2001/2223* (2013.01); *G01N 2015/0046* (2013.01); *G01N 2015/0065* (2013.01)

(56) References Cited

U.S. PATENT DOCUMENTS

| | | | | |
|---|---|---|---|---|
| 5,855,652 A | * | 1/1999 | Talley | B03C 3/014 |
| | | | | 95/60 |
| 6,777,228 B2 | * | 8/2004 | Lejeune | G01N 1/2273 |
| | | | | 435/288.6 |
| 7,006,923 B1 | * | 2/2006 | Rubin | G01N 15/1463 |
| | | | | 702/19 |
| 8,524,482 B1 | * | 9/2013 | Wick | C12N 7/00 |
| | | | | 424/184.1 |
| 2003/0159498 A1 | * | 8/2003 | Small | G01H 3/00 |
| | | | | 73/24.02 |
| 2004/0089156 A1 | * | 5/2004 | Gartstein | B03C 3/16 |
| | | | | 96/53 |
| 2005/0274206 A1 | * | 12/2005 | Coyle | G01N 1/2208 |
| | | | | 73/864.71 |
| 2007/0234901 A1 | * | 10/2007 | Pletcher | B03C 3/011 |
| | | | | 95/78 |
| 2010/0001184 A1 | * | 1/2010 | Chen | G01N 15/0266 |
| | | | | 250/307 |
| 2010/0186524 A1 | * | 7/2010 | Ariessohn | G01N 1/2202 |
| | | | | 73/863.22 |
| 2010/0242632 A1 | * | 9/2010 | Call | B07B 7/00 |
| | | | | 73/863.22 |
| 2012/0154348 A1 | * | 6/2012 | Okuno | C12Q 1/06 |
| | | | | 345/204 |
| 2014/0017723 A1 | * | 1/2014 | Hwang | G01N 1/2202 |
| | | | | 435/34 |
| 2015/0099272 A1 | * | 4/2015 | Hwang | C12Q 1/04 |
| | | | | 435/34 |

FOREIGN PATENT DOCUMENTS

| | | |
|---|---|---|
| KR | 10-0811199 B1 | 2/2008 |
| KR | 10-2012-0030362 A | 3/2012 |
| KR | 10-1179039 B1 | 9/2012 |
| KR | 10-2013-0038356 A | 4/2013 |

* cited by examiner

APPARATUS FOR IN REAL TIME DETECTING BIOLOGICAL PARTICLE AND NON-BIOLOGICAL PARTICLE IN THE ATMOSPHERE AND METHOD FOR DETECTING BIOLOGICAL PARTICLE AND NON-BIOLOGICAL PARTICLE USING THE SAME

BACKGROUND OF THE INVENTION

Field of the Invention

The present invention relates to an apparatus for in real time detecting biological particles and non-biological particles in the atmosphere and a method for detecting biological particles and non-biological particles using the same, and more particularly, to an apparatus for in real time detecting biological particles and non-biological particles in the atmosphere and a method for detecting biological particles and non-biological particles using the same that are capable of detecting the biological particles and non-biological particles suspended in the atmosphere in real time.

Background of the Related Art

As interest in environmental pollution goes up, recently, many developments for air cleaners removing environmental pollution particles from the air and lots of studies on the sampling, analysis and detection on virus particles have been dynamically made.

Accordingly, sampling devices for virus particles have been needed recently so as to measure the sizes, shapes, materials and distribution concentrations of viruses.

Current environmental standard is applied only for particles more than 10 µm, but since much damage is really caused by fine particles under 10 µm, studies on the fine particles have been continuously made.

However, just one pollutant is detected with single equipment for measuring biological particles and non-biological particles, and since the equipment has a high price and a large size, further, it is very difficult to move the equipment to a place on which the virus particles suspended in the atmosphere are detected. Generally, the biological particles include viruses, flower powder, fungal spores and so on, and the non-biological particles include fine particles, dust, nitrogen oxide particles, sulfur dioxide gas particles, automobile exhaust gas particles and so on.

So as to measure the virus particles suspended in the atmosphere, further, separate collection and cultivation should be measured for a long period of time over 24 hours, and the measurement is conducted through batch-type analysis, thus having many problems in the utilization thereof.

In more detail, FIG. 1 is a flowchart showing a conventional method for measuring an object through the cultivation of the object, and FIG. 2 is a photograph showing a fluorescence microscope used in a conventional method wherein an object to be measured is dyed and observed by the fluorescence microscope. As shown, a cultivation method wherein microorganism is cultivated and measured and a dyeing method wherein microorganism is dyed and observed by the fluorescence microscope have been generally adopted in conventional practice.

According to the measurement methods in the conventional practice, however, the microorganism suspended in the atmosphere cannot be detected directly from the air, thus requiring a series of manual operations including separate sampling and pre-treatments.

SUMMARY OF THE INVENTION

Accordingly, the present invention has been made in view of the above-mentioned problems occurring in the prior art, and it is an object of the present invention to provide an apparatus for in real time detecting biological particles and non-biological particles in the atmosphere and a method for detecting biological particles and non-biological particles using the same that are provided with an impactor adapted to sort the biological particles and non-biological particles by size and a separator adapted to sort the biological particles and non-biological particles having different charge quantities from each other, thus allowing the biological particles and non-biological particles suspended in the atmosphere to be detected in real time and enabling the detection to be rapidly conducted on a site on which the detection is conducted, without having any series of manual operations including separate sampling and pre-treatments.

To accomplish the above-mentioned object, according to a first aspect of the present invention, there is provided an apparatus for in real time detecting biological particles and non-biological particles in the atmosphere, the apparatus including: an impactor adapted to sort the biological particles and non-biological particles absorbed from the outside by size; a charger adapted to charge the biological particles and non-biological particles sorted by means of the impactor to specific charge (positive or negative charge); a separator adapted to introduce the biological particles and non-biological particles charged by the charger thereinto and to sort the biological particles and non-biological particles charged to different charge quantities from each other by using given air flow and electric force; and a particle measurement sensor mounted on an outlet discharging the biological particles and non-biological particles sorted through the separator therefrom so as to measure the concentrations of the particles discharged from the outlet.

According to the present invention, preferably, the apparatus further includes a compressed air supplier adapted to supply compressed air transporting the biological particles and non-biological particles suspended in the atmosphere therefrom.

According to the present invention, preferably, the impactor includes: an introduction channel adapted to receive the biological particles and non-biological particles from the outside; an auxiliary flow channel disposed in the same direction as the flow direction of the particles introduced into the introduction channel; and one or more main flow channels disposed in a vertical direction with respect to the flow direction of the particles introduced into the introduction channel.

According to the present invention, preferably, the charger is formed of a charger using corona discharge.

According to the present invention, preferably, the charger includes: a housing having an introduction portion adapted to introduce the biological particles and non-biological particles supplied from the impactor thereinto and a discharge portion adapted to discharge the charged biological particles and non-biological particles therefrom; a charge electrode disposed inside the housing in such a manner as to allow the biological particles and non-biological particles flowing along the interior of the housing to be charged by means of a given voltage applied thereto; and a ground electrode disposed on the inner periphery of the housing in such a manner as to be spaced apart from the charge electrode by a given distance, while having a grounded structure.

According to the present invention, preferably, the separator includes: a compressed air inlet formed on one end of a flow pipe to introduce the compressed air supplied from the compressed air supplier thereinto; a particle inlet formed on one end of the flow pipe to introduce the charged biological particles and non-biological particles thereinto; a first outlet and the second outlet formed on the other end of the flow pipe in such a manner as to be opposed to each other in a perpendicular direction with respect to the longitudinal direction of the flow pipe; the flow pipe having one end on which the compressed air inlet and the particle inlet are formed and the other end on which the first outlet and the second outlet are formed and a flow path formed therein to allow the biological particles and the non-biological particles to flow therealong; and a first charged electrode plate and a second charged electrode plate disposed on the side periphery of the flow pipe in such a manner as to be opposed to each other and charged to different polarities from each other.

According to the present invention, preferably, the separator further includes a protrusion formed between the first outlet and the second outlet in such a manner as to protrude inward from the flow pipe by a given length.

To accomplish the above-mentioned object, according to a second aspect of the present invention, there is provided an apparatus for in real time detecting biological particles and non-biological particles in the atmosphere, the apparatus including: a first impactor adapted to sort the biological particles and non-biological particles supplied from the outside to discharge the biological particles and non-biological particles having diameters larger than a first particle diameter to the outside and to supply the biological particles and non-biological particles having diameters smaller than the first particle diameter to a second impactor; the second impactor adapted to sort the biological particles and non-biological particles supplied from the first impactor to supply the biological particles and non-biological particles having diameters larger than a second particle diameter to a first charger and to supply the biological particles and non-biological particles having diameters smaller than the second particle diameter to a third impactor; the third impactor adapted to sort the biological particles and non-biological particles supplied from the second impactor to supply the biological particles and non-biological particles having diameters larger than a third particle diameter to a second charger and to supply the biological particles and non-biological particles having diameters smaller than the second particle diameter to a third charger; the first charger adapted to charge the biological particles and non-biological particles sorted by means of the second impactor to specific charge (positive or negative charge); the second charger and the third charger adapted to charge the biological particles and non-biological particles sorted by means of the third impactor to specific charge (positive or negative charge); a first separator adapted to introduce the biological particles and non-biological particles charged by the first charger thereinto and to sort the biological particles and non-biological particles charged to different charge quantities from each other by using given air flow and electric force; a second separator adapted to introduce the biological particles and non-biological particles charged by the second charger thereinto and to sort the biological particles and non-biological particles charged to different charge quantities from each other by using given air flow and electric force; a third separator adapted to introduce the biological particles and non-biological particles charged by the third charger thereinto and to sort the biological particles and non-biological particles charged to different charge quantities from each other by using given air flow and electric force; and first, second and third particle measurement sensors mounted on outlets each discharging the biological particles and non-biological particles sorted through the first separator, the second separator and the third separator therefrom so as to measure the concentrations of the particles discharged from the outlets.

According to the present invention, preferably, the apparatus further includes a compressed air supplier adapted to supply compressed air transporting the biological particles and non-biological particles suspended in the atmosphere therefrom.

According to the present invention, preferably, each of the first impactor, the second impactor and the third impactor includes: an introduction channel adapted to receive the biological particles and non-biological particles from the outside, an auxiliary flow channel disposed in the same direction as the flow direction of the particles introduced into the introduction channel; and one or more main flow channels disposed in a vertical direction with respect to the flow direction of the particles introduced into the introduction channel.

According to the present invention, preferably, each of the first charger, the second charger and the third charger is formed of a charger using corona discharge.

According to the present invention, preferably, each of the first charger, the second charger and the third charger includes: a housing having an introduction portion adapted to introduce the biological particles and non-biological particles supplied from the impactor thereinto and a discharge portion adapted to discharge the charged biological particles and non-biological particles therefrom; a charge electrode disposed inside the housing in such a manner as to allow the biological particles and non-biological particles flowing along the interior of the housing to be charged by means of a given voltage applied thereto; and a ground electrode disposed on the inner periphery of the housing in such a manner as to be spaced apart from the charge electrode by a given distance, while having a grounded structure.

According to the present invention, preferably, each of the first separator, the second separator and the third separator includes: a compressed air inlet formed on one end of a flow pipe to introduce the compressed air supplied from the compressed air supplier thereinto; a particle inlet formed on one end of the flow pipe to introduce the charged biological particles and non-biological particles thereinto; a first outlet and the second outlet formed on the other end of the flow pipe in such a manner as to be opposed to each other in a perpendicular direction with respect to the longitudinal direction of the flow pipe; the flow pipe having one end on which the compressed air inlet and the particle inlet are formed and the other end on which the first outlet and the second outlet are formed and a flow path formed therein to allow the biological particles and the non-biological particles to flow therealong; and a first charged electrode plate and a second charged electrode plate disposed on the side periphery of the flow pipe in such a manner as to be opposed to each other and charged to different polarities from each other.

According to the present invention, preferably, each of the first separator, the second separator and the third separator further includes a protrusion formed between the first outlet and the second outlet in such a manner as to protrude inward from the flow pipe by a given length.

To accomplish the above-mentioned object, according to a third aspect of the present invention, there is provided a method for detecting biological particles and non-biological particles using an apparatus according to the first aspect of the present invention, the method including the steps of: absorbing the biological particles and non-biological particles suspended in the atmosphere, together with air, through the impactor; sorting the biological particles and non-biological particles in the atmosphere absorbed from the outside by size by means of the impactor; charging the biological particles and non-biological particles sorted by the impactor to specific charge (positive or negative charge) through the charger; charging the biological particles and non-biological particles charged by the charger to different charge quantities and sorting the biological particles and non-biological particles charged to the different charge quantities through the separator; and measuring the concentrations of the particles sorted by the separator through the particle measurement sensor.

To accomplish the above-mentioned object, according to a fourth aspect of the present invention, there is provided a system for in real time detecting biological particles and non-biological particles suspended in the atmosphere, the system comprising: an apparatus according to the first aspect of the present invention; a controller controlling the driving of the apparatus; a data calculator connected to the particle measurement sensor and adding up the concentrations of the particles detected by the particle measurement sensor to calculate the result data; and a display screen displaying the result data calculated from the data calculator.

According to the present invention, preferably, the system is formed of a portable integral type module.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Hereinafter, an explanation on an apparatus for in real time detecting biological particles and non-biological particles in the atmosphere and a method for detecting biological particles and non-biological particles using the same according to the present invention will be in detail given with reference to the attached drawing. The present invention is disclosed with reference to the attached drawing, but if it is determined that the detailed explanation on the well known technology related to the present invention makes the scope of the present invention not clear, the explanation will be avoided for the brevity of the description.

Figure 1:
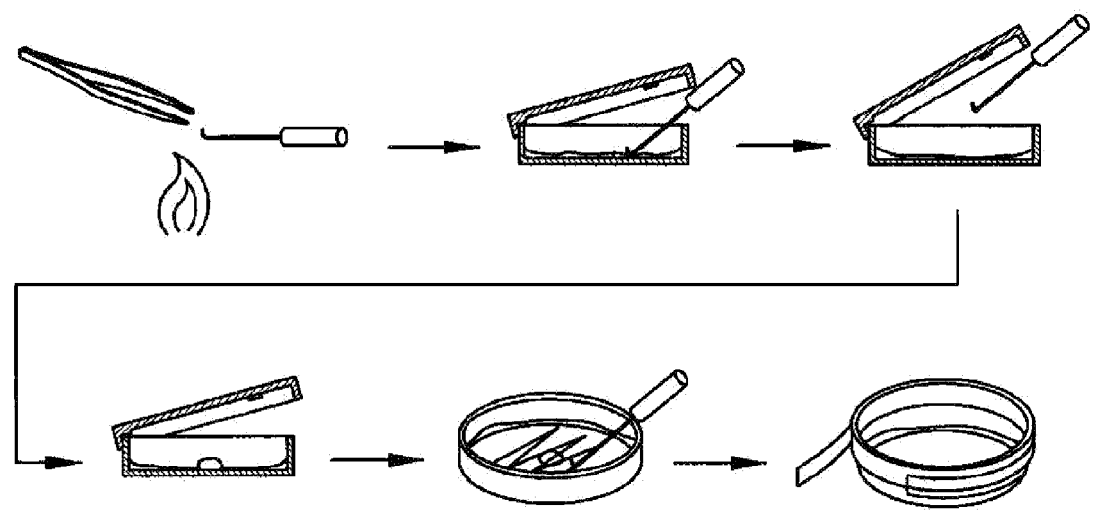
FIG. 1 is a flowchart showing a conventional method for measuring an object through the cultivation of the object.
Figure 2:
FIG. 2 is a photograph showing a fluorescence microscope used in a conventional method wherein an object to be measured is dyed and observed by the fluorescence microscope.
Figure 3:
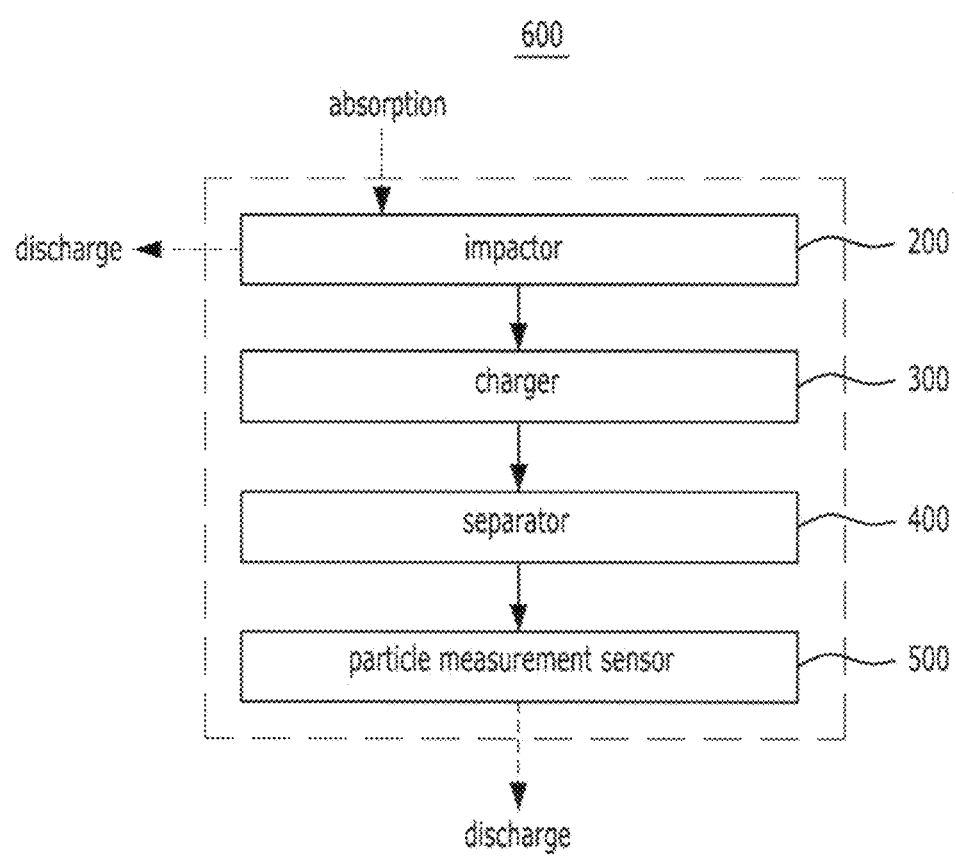
FIG. 3 is a block diagram showing an apparatus for in real time detecting biological particles and non-biological particles in the atmosphere according to a first embodiment of the present invention.

FIG. 3 is a block diagram showing an apparatus for in real time detecting biological particles and non-biological particles in the atmosphere according to a first embodiment of the present invention.

As shown in FIG. 3, an apparatus 600 for in real time detecting biological particles and non-biological particles in the atmosphere according to a first embodiment of the present invention includes an impactor 200, a charger 300, a separator 400, and a particle measurement sensor 500.

In more detail, the impactor 200 has a structure of sorting the biological particles and non-biological particles absorbed from the outside by size. So as to allow the biological particles and non-biological particles suspended in the atmosphere to be absorbed into the impactor 200, a pump, which absorbs air at a given pressure, may be mounted on the rear end portion of the particle measurement sensor 500. Of course, the pump may be replaced with other devices capable of allowing the biological particles and non-biological particles to be absorbed into the impactor 200 from the outside.

Further, the charger 300 has a structure of charging the particles sorted by means of the impactor 200 to specific charge (positive or negative charge).

The separator 400 has a structure of introducing the charged particles from the charger 300 and sorting the charged particles having different charge quantities from each other by means of given air flow and electric force.

The particle measurement sensor 500 is mounted on an outlet from which the sorted particles through the separator 400 are discharged so as to measure the concentrations of the particles discharged from the outlet.

Accordingly, the apparatus 600 for in real time detecting the biological particles and non-biological particles according to the first embodiment of the present invention is provided with the impactor 200 adapted to sort the biological particles and the non-biological particles by size and the separator 400 adapted to sort the charged biological particles and non-biological particles from each other, thus allowing the biological particles and non-biological particles suspended in the atmosphere to be detected in real time.

Now, an explanation on each part constituting the apparatus 600 for in real time detecting the biological particles and non-biological particles according to the first embodiment of the present invention will be in detail given.

Figure 4:
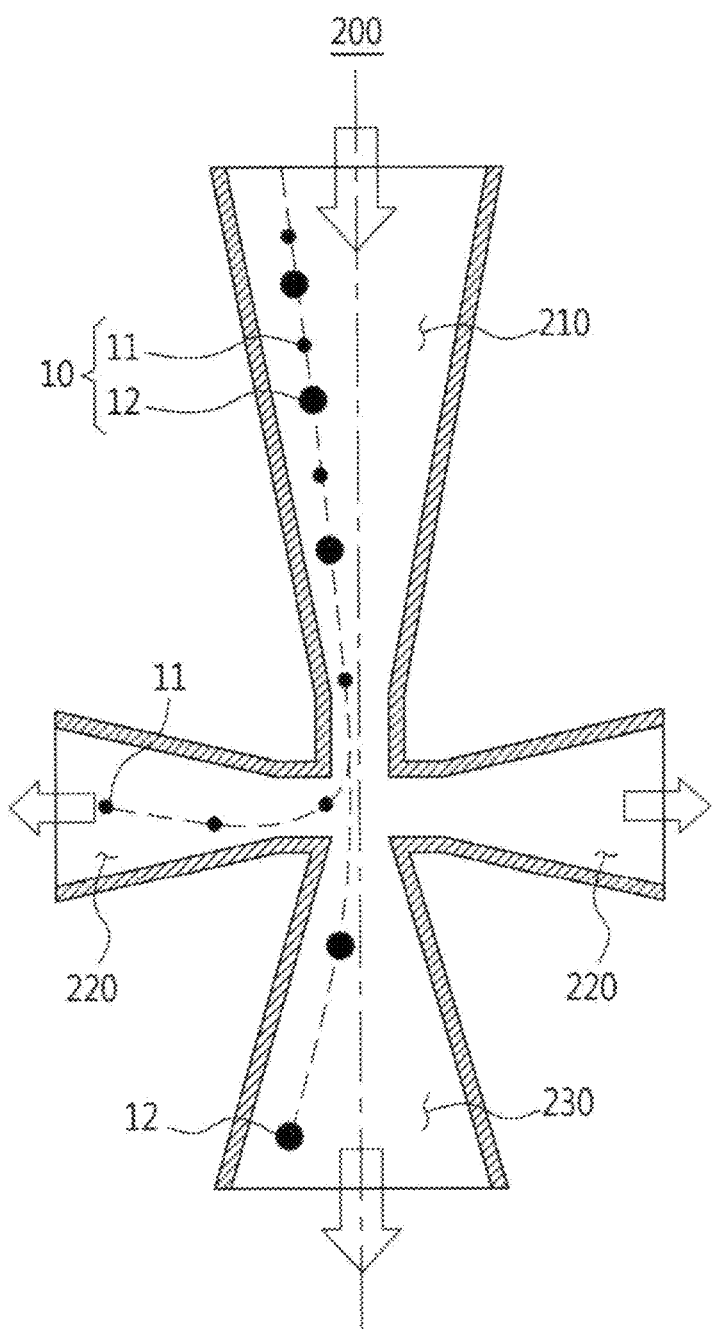
FIG. 4 is a diagram showing an impactor of FIG. 3.

FIG. 4 is a diagram showing the impactor of FIG. 3.

As shown in FIG. 4, the impactor 200 of the apparatus 600 according to the first embodiment of the present invention includes an introduction channel 210, an auxiliary flow channel 230 and main flow channels 220. In more detail, the introduction channel 210 is adapted to receive the biological particles and non-biological particles from an absorber 100, the auxiliary flow channel 230 is disposed in the same direction as the flow direction of the particles introduced into the introduction channel 210, and the main flow channels 220 are disposed in a vertical direction with respect to the flow direction of the particles introduced into the introduction channel 210.

Under the above-mentioned configuration, the impactor 200 sorts biological particles 12 and non-biological particles 11 supplied from the introduction channel 210 by size. In more detail, the biological particles 12 having relatively large sizes are introduced into the introduction channel 210 and do not flow along the main flow channels 220 by means of the inertial force flowing along the introduction channel 210, and the biological particles 11 having relatively small sizes are introduced into the introduction channel 210 and flow along the main flow channels 220 by means of the inertial force flowing along the introduction channel 210. Accordingly, the impactor 200 can sort the particles by size.

Figure 5:
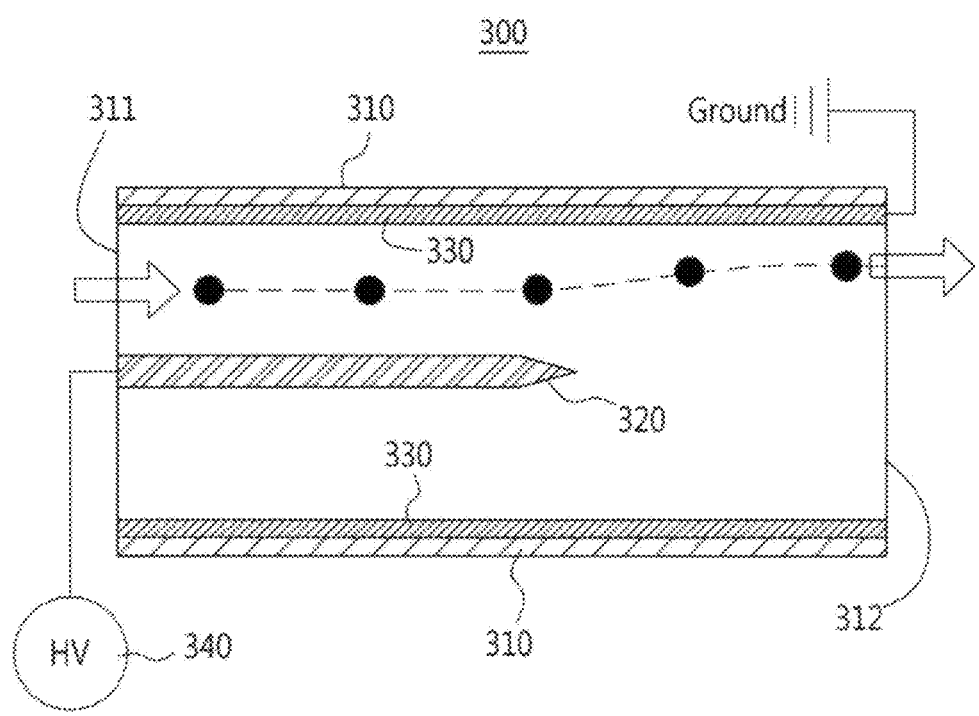
FIG. 5 is a diagram showing a charger of FIG. 3.

FIG. 5 is a diagram showing the charger of FIG. 3.

As shown in FIG. 5, the charger 300 of the apparatus 600 according to the first embodiment of the present invention is not specially limited only if it charges the particles to specific charge (positive or negative charge). For example, the charger 300 may be formed of a charger using corona discharge or a plasma ion generator.

According to the present invention, in more detail, the charger 300 includes a housing 310, a charge electrode 320, and a ground electrode 330.

The housing 310 has an introduction portion 311 adapted to introduce the biological particles and non-biological particles supplied from the impactor 200 thereinto and a discharge portion 312 adapted to discharge the charged biological particles and non-biological particles therefrom.

The charge electrode 320 is disposed inside the housing 310 in such a manner as to allow the biological particles and non-biological particles flowing along the interior of the housing 310 to be charged by means of a given high voltage 340 applied thereto.

Further, the ground electrode 330 is disposed on the inner periphery of the housing 310 in such a manner as to be spaced apart from the charge electrode 320 by a given distance, while having a grounded structure.

According to the present invention, therefore, the charger 300 can charge the biological particles and non-biological particles supplied from the impactor 200 to specific charge (positive or negative charge).

In detail, the biological particles and non-biological particles sorted to the same sizes as each other by means of the impactor 200 are charged to specific charge (positive or negative charge) in such a manner as to have different charge quantities from each other. In more detail, the charge quantities of the biological particles are larger than those of the non-biological particles because of a difference between the conductivities of the surfaces of the biological particles and non-biological particles.

Figure 6:
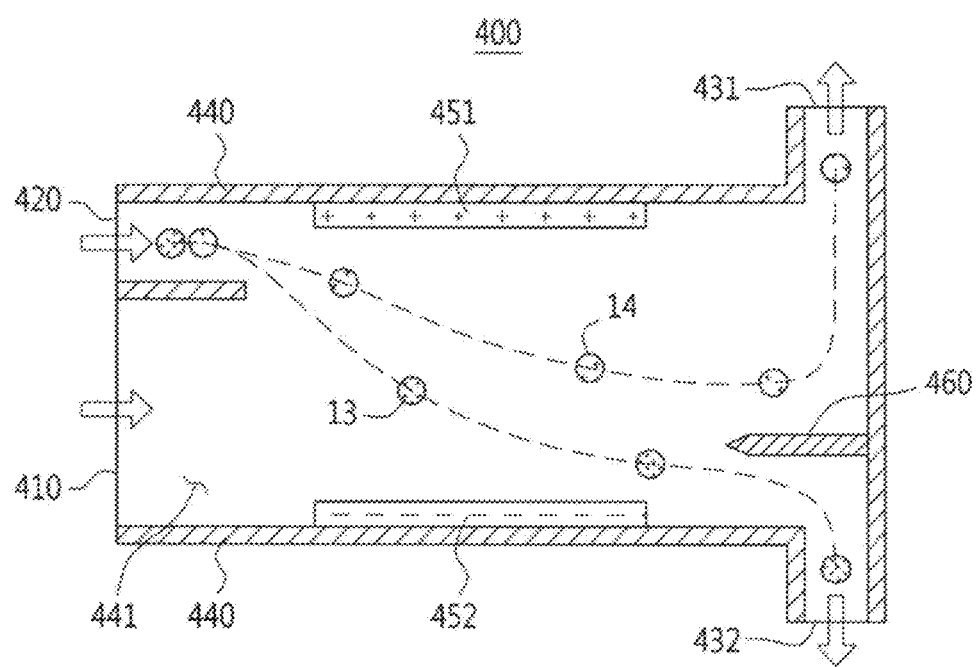
FIG. 6 is a diagram showing a separator of FIG. 3.

FIG. 6 is a diagram showing the separator of FIG. 3.

As shown in FIG. 6, the separator 400 of the apparatus 600 according to the first embodiment of the present invention includes a compressed air inlet 410, a particle inlet 420, a first outlet 431, a second outlet 432, a flow pipe 440, a first charged electrode plate 451, and a second charged electrode plate 452.

In detail, the compressed air inlet 410 is formed on one end of the flow pipe 440 to introduce the compressed air supplied from the compressed air supplier 110 thereinto, and the particle inlet 420 is formed on one end of the flow pipe 440 to introduce the charged biological particles and non-biological particles thereinto. Further, the first outlet 431 and the second outlet 432 are formed on the other end of the flow pipe 440 in such a manner as to be opposed to each other in a perpendicular direction with respect to the longitudinal direction of the flow pipe 440, and the flow pipe 440 has one end on which the compressed air inlet 410 and the particle inlet 420 are formed and the other end on which the first outlet 431 and the second outlet 432 are formed and a flow path 441 formed therein to allow the biological particles and the non-biological particles to flow therealong. Furthermore, the first charged electrode plate 451 and the second charged electrode plate 452 are disposed on the side periphery of the flow pipe 440 in such a manner as to be opposed to each other and charged to different polarities from each other.

In some cases, as shown in FIG. 6, the separator 400 further includes a protrusion 460 formed between the first outlet 431 and the second outlet 432 in such a manner as to protrude inward from the flow pipe 440 by a given length. In this case, the sorting efficiency for the charged biological particles 13 and the charged non-biological particles 14 can be improved.

As mentioned above, the biological particles and the non-biological particles 14 charged with the different charge quantities from each other are sortedly discharged through the first outlet 431 and the second outlet 432 by means of the separator 400 in which an electric field is formed.

In detail, as shown in FIG. 6, the biological particles 13 charged with the relatively larger charge quantities when compared with the non-biological particles 14 are attracted by the electric field formed by the separator 400 and thus discharged through the second outlet 432, whereas the non-biological particles 14 charged with the relatively smaller charge quantities when compared with the biological particles 13 are discharged through the first outlet 431.

So as to improve the accuracy of sorting between the biological particles 13 and the non-biological particles 14, the flow rate of the compressed air introduced from the compressed air inlet 410 can be controlled. So as to improve the accuracy of sorting between the biological particles 13 and the non-biological particles 14, further, the size of the electric field generated between the first charged electrode plate 451 and the second charged electrode plate 452 can be controlled.

Accordingly, the apparatus 600 for in real time detecting the biological particles and non-biological particles according to the first embodiment of the present invention is provided with the impactor 200 adapted to sort the biological particles and the non-biological particles by size and the separator 400 adapted to sort the charged biological particles and non-biological particles from each other, thus allowing the biological particles and non-biological particles suspended in the atmosphere to be detected in real time.

Figure 7:
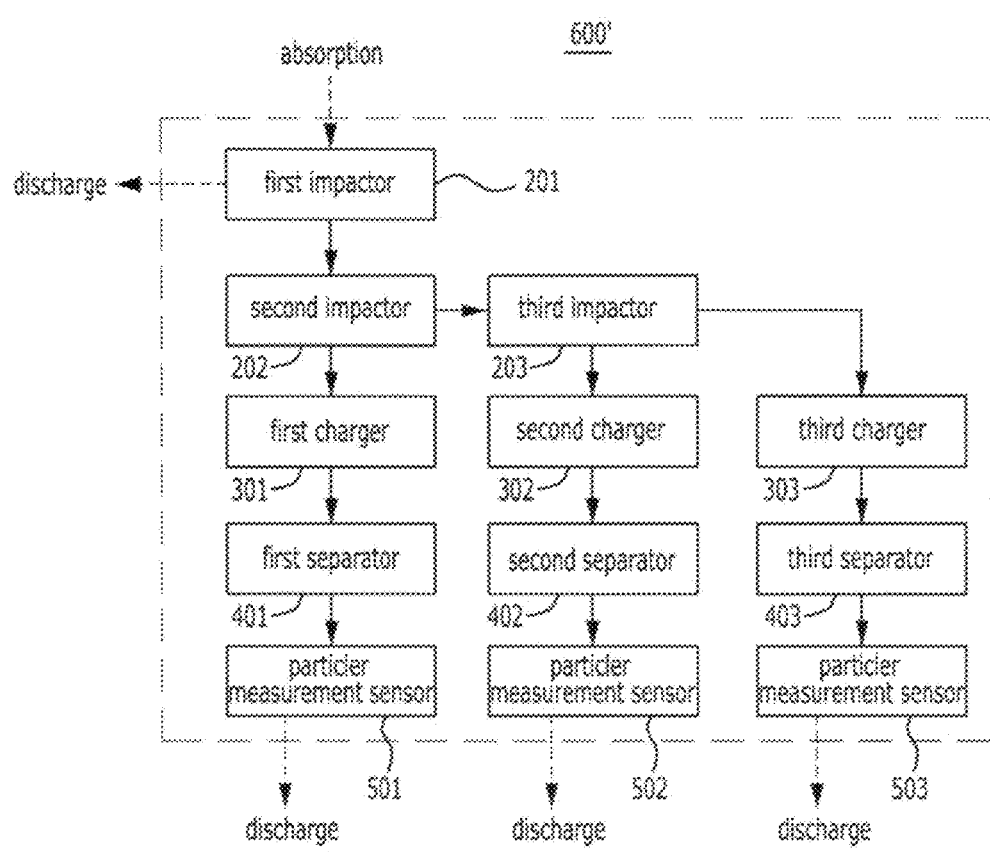
FIG. 7 is a block diagram showing an apparatus for in real time detecting biological particles and non-biological particles in the atmosphere according to a second embodiment of the present invention.

FIG. 7 is a block diagram showing an apparatus for in real time detecting biological particles and non-biological particles in the atmosphere according to a second embodiment of the present invention.

As shown in FIG. 7, an apparatus 600' for in real time detecting biological particles and non-biological particles in the atmosphere according to the second embodiment of the present invention includes first to third impactors 201 to 203, first to third chargers 301 to 303, first to third separators 401 to 403 and a plurality of particle measurement sensors 501 to 503, unlike the apparatus 600 according to the first embodiment of the present invention that has one impactor 200, one charger 300, one separator 400 and one particle measurement sensor 500.

A detailed explanation on each part constituting the apparatus 600' having the same functions as that in the apparatus 600 according to the first embodiment of the present invention will be avoided for the brevity of the description.

The apparatus 600' for in real time detecting biological particles and non-biological particles according to the second embodiment of the present invention is provided with the first to third impactors 201 to 203, thus allowing the particle sizes to be sorted more finely.

That is, the first impactor 201 sorts the biological particles and non-biological particles supplied from the outside to discharge the biological particles and non-biological particles having diameters larger than a first particle diameter to the outside and to supply the biological particles and non-biological particles having diameters smaller than the first particle diameter to the second impactor 202. Further, the second impactor 202 sorts the biological particles and non-biological particles supplied from the first impactor 201 to supply the biological particles and non-biological particles having diameters larger than a second particle diameter to the first charger 301 and to supply the biological particles and non-biological particles having diameters smaller than the second particle diameter to the third impactor 203. Furthermore, the third impactor 203 sorts the biological particles and non-biological particles supplied from the second impactor 202 to supply the biological particles and non-biological particles having diameters larger than a third particle diameter to the second charger 302 and to supply the biological particles and non-biological particles having diameters smaller than the second particle diameter to the third charger 303.

Under the above configuration, accordingly, the apparatus 600' for in real time detecting biological particles and non-biological particles according to the second embodiment of the present invention can sort and detect the biological particles and the non-biological particles by size more finely.

Figure 8:
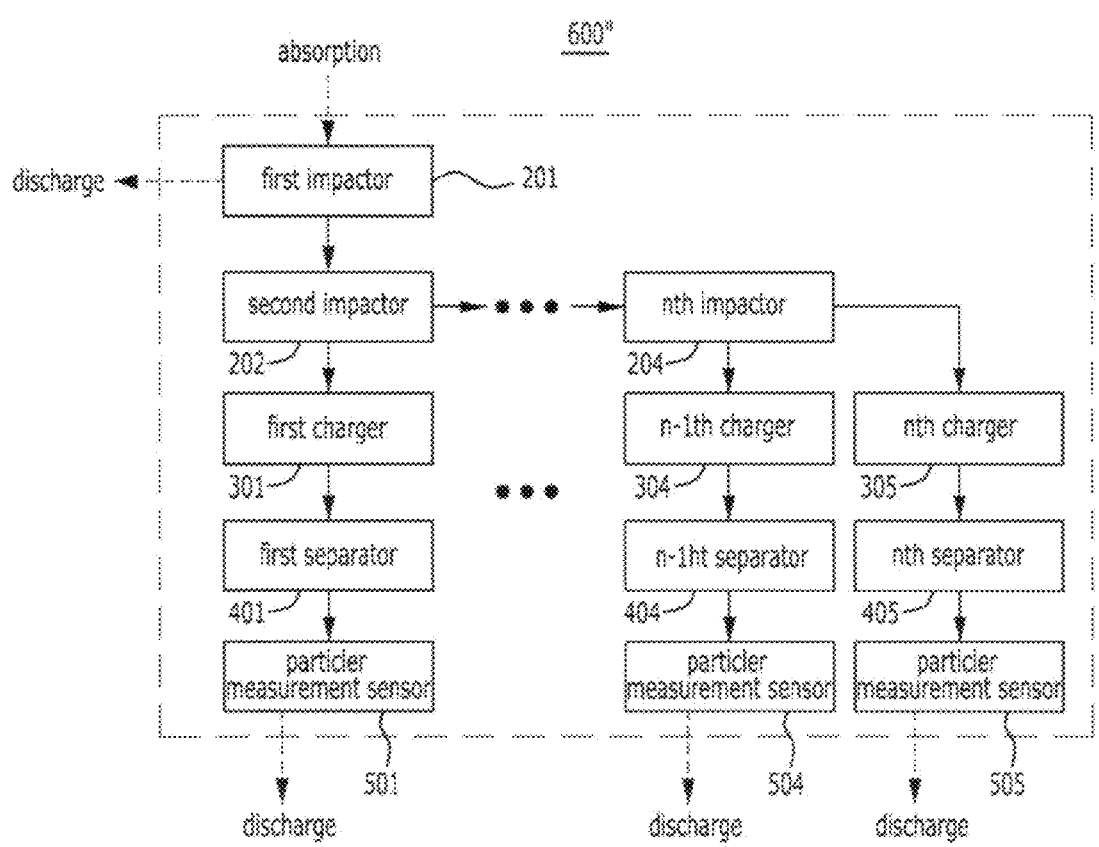
FIG. 8 is a block diagram showing an apparatus for in real time detecting biological particles and non-biological particles in the atmosphere according to a third embodiment of the present invention.

FIG. 8 is a block diagram showing an apparatus for in real time detecting biological particles and non-biological particles in the atmosphere according to a third embodiment of the present invention.

As shown in FIG. 8, an apparatus 600" for in real time detecting biological particles and non-biological particles in the atmosphere according to the third embodiment of the present invention includes first to nth impactors 201 to 204, first to nth chargers 301 to 305, first to nth separators 401 to 405, and a plurality of particle measurement sensors 501 to 505, unlike the apparatuses 600 and 600' according to the first and second embodiments of the present invention.

Like the apparatus 600' according to the second embodiment of the present invention, the apparatus 600" for in real time detecting biological particles and non-biological particles according to the third embodiment of the present invention is provided with the first to nth impactors 201 to 204, thus allowing the particle sizes to be sorted more finely. The above-mentioned configuration of the apparatus 600" may be changed in accordance with a designer's design intention or an operator's detection intention.

Accordingly, the apparatus 600" according to the third embodiment of the present invention can detect the biological particles and non-biological particles suspended in the atmosphere in real time according to the particle sizes sorted more finely.

Figure 9:
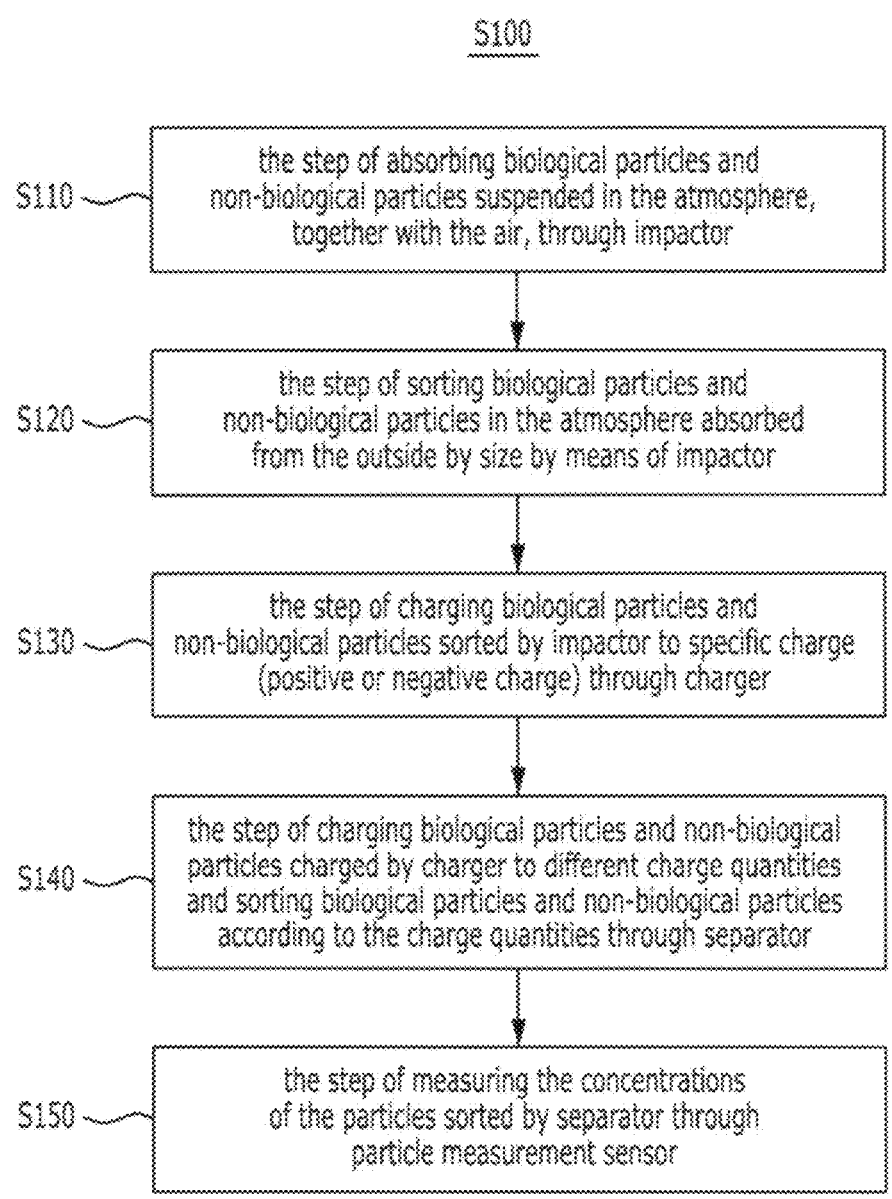
FIG. 9 is a flowchart showing a method for detecting biological particles and non-biological particles using the apparatus according to the present invention.

FIG. 9 is a flowchart showing a method for detecting biological particles and non-biological particles using the apparatus according to the present invention.

As shown in FIG. 9, the method for detecting biological particles and non-biological particles using the apparatus 600 as shown in FIG. 3 includes the step S110 of absorbing the biological particles and non-biological particles suspended in the atmosphere, together with air, through the impactor 200. In more detail, a pump, which absorbs air at a given pressure, is mounted on the rear end portion of the particle measurement sensor 500 so as to allow the biological particles and non-biological particles suspended in the atmosphere to be absorbed into the impactor 200. Of course, the pump may be replaced with other devices capable of allowing the biological particles and non-biological particles to be absorbed into the impactor 200 from the outside.

Next, the method for detecting biological particles and non-biological particles according to the present invention includes the step S120 of sorting the biological particles and non-biological particles in the atmosphere absorbed from the outside by size by means of the impactor 200 and the step S130 of charging the biological particles and non-biological particles sorted by the impactor 200 to specific charge (positive or negative charge) through the charger 300.

After that, the method for detecting biological particles and non-biological particles according to the present invention includes the step S140 of charging the biological particles and non-biological particles charged by the charger 300 to different charge quantities and sorting the biological particles and non-biological particles charged to the different charge quantities through the separator 400 and the step S150 of measuring the concentrations of the particles sorted by the separator 400 through the particle measurement sensor 500.

According to the method for in real time detecting the biological particles and non-biological particles, the biological particles and the non-biological particles are detected rapidly on a site on which the detection is conducted because no series of manual operations including separate sampling and pre-treatments are required.

Figure 10:
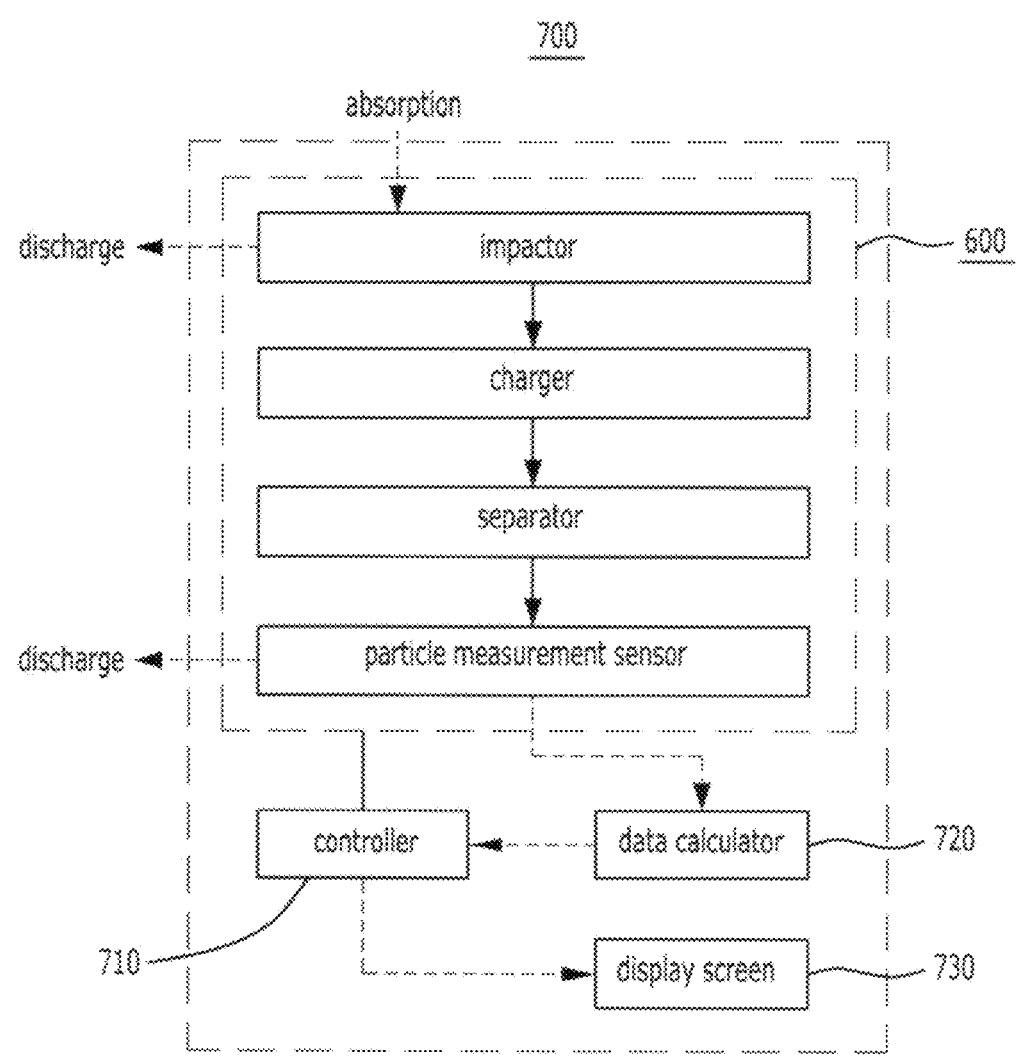
FIG. 10 is a block diagram showing a system for in real time detecting biological particles and non-biological particles in the atmosphere according to an embodiment of the present invention.
Figure 11:
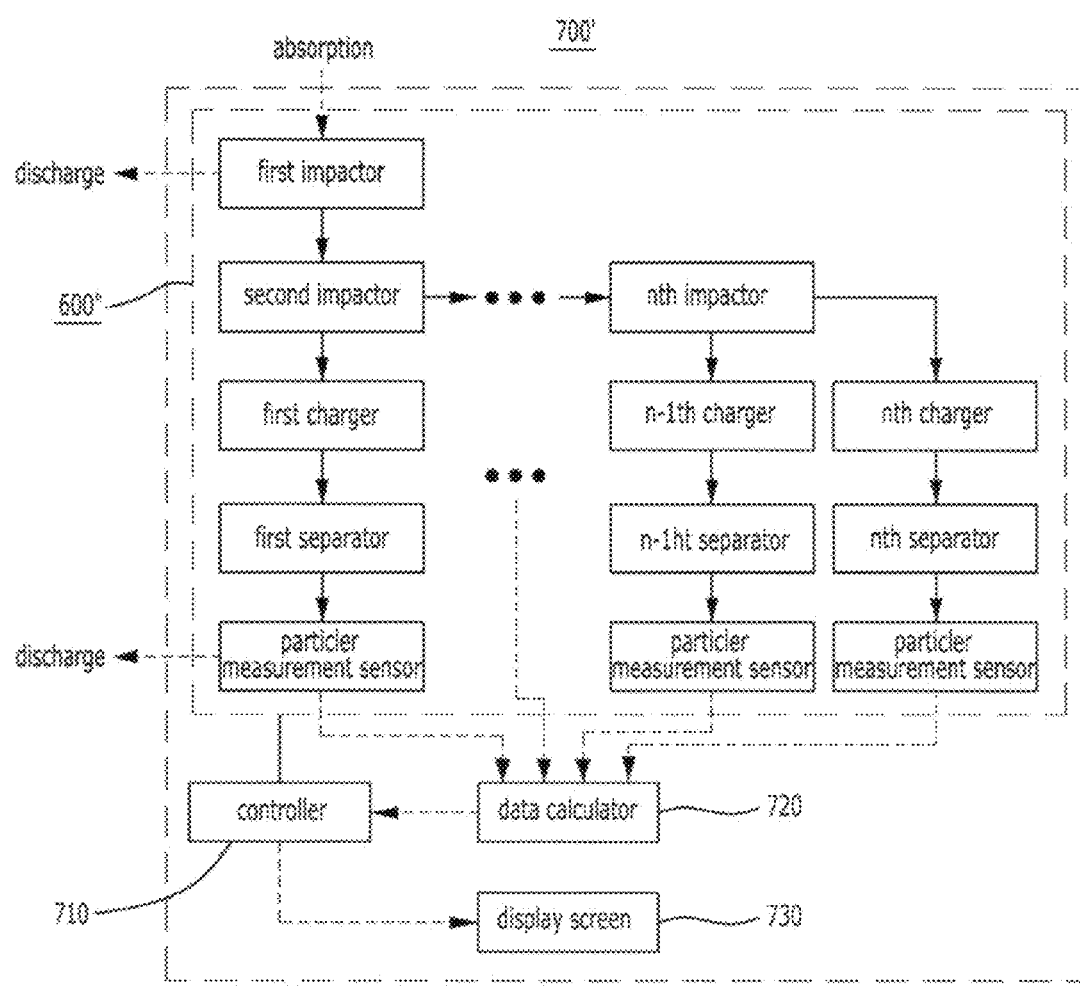
FIG. 11 is a block diagram showing a system for in real time detecting biological particles and non-biological particles in the atmosphere according to another embodiment of the present invention.

FIG. 10 is a block diagram showing a system for in real time detecting biological particles and non-biological particles in the atmosphere according to an embodiment of the present invention, and FIG. 11 is a block diagram showing a system for in real time detecting biological particles and non-biological particles in the atmosphere according to another embodiment of the present invention.

As shown in FIG. 10, a system 700 for in real time detecting biological particles and non-biological particles in the atmosphere according to an embodiment of the present invention includes the apparatus 600 as shown in FIG. 3, a controller 710 controlling the driving of the apparatus 600, a data calculator 720 connected to the particle measurement sensor 500 and adding up the concentrations of the particles detected by the particle measurement sensor to calculate the result data, and a display screen 730 displaying the result data calculated from the data calculator 720.

As shown in FIG. 11, a system 700' for in real time detecting biological particles and non-biological particles in the atmosphere according to another embodiment of the present invention includes the apparatus 600" as shown in FIG. 8, a controller 710 controlling the driving of the apparatus 600", a data calculator 720 connected to the particle measurement sensors 501, 504 and 505 and adding up the concentrations of the particles detected by the particle measurement sensors to calculate the result data, and a display screen 730 displaying the result data calculated from the data calculator 720.

In some cases, the systems 700 and 700' for in real time detecting biological particles and non-biological particles according to the embodiments of the present invention may be formed of a portable integral type module.

Accordingly, the systems 700 and 700' for in real time detecting biological particles and non-biological particles according to the embodiments of the present invention can detect the biological particles and the non-biological particles rapidly on a site on which the detection is conducted because no series of manual operations including separate sampling and pre-treatments are required.

As described above, the apparatus for in real time detecting the biological particles and non-biological particles is provided with the impactor adapted to sort the biological particles and the non-biological particles by size and the separator adapted to sort the charged biological particles and non-biological particles from each other, thus allowing the biological particles and non-biological particles suspended in the atmosphere to be detected in real time.

Further, the apparatus for in real time detecting the biological particles and non-biological particles is configured wherein the impactor sorting the biological particles and the non-biological particles by size and the separator sorting the charged biological particles and non-biological particles from each other are mounted on the single apparatus, thus requiring no series of manual operations including separate sampling and pre-treatments.

Furthermore, according to the apparatus and method for in real time detecting the biological particles and non-biological particles, the biological particles and the non-biological particles are detected rapidly on a site on which the detection is conducted because no series of manual operations including separate sampling and pre-treatments are required.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An apparatus (600) for in real time detecting biological particles and non-biological particles in the atmosphere, the apparatus comprising:

an impactor (200) adapted to sort the biological particles and non-biological particles absorbed from the outside by size;

a charger (300) adapted to charge the biological particles and non-biological particles sorted by means of the impactor (200) to specific charge (positive or negative charge);

a separator (400) adapted to introduce the biological particles and non-biological particles charged by the charger (300) thereinto and to sort the biological particles and non-biological particles charged to different charge quantities from each other by using predetermined air flow and electric force; and a particle measurement sensor (500) mounted on an outlet discharging the biological particles and non-biological particles sorted through the separator (400) therefrom so as to measure the concentrations of the particles discharged from the outlet, wherein the separator (400) comprises:

a compressed air inlet (410) formed on one end of a flow pipe (440) to introduce the compressed air supplied from the compressed air supplier 110) thereinto;

a particle inlet (420) formed on one end of the flow pipe (440) to introduce the charged biological particles and non-biological particles thereinto;

a first outlet (431) and the second outlet (432) formed on the other end of the flow pipe (440) in such a manner as to be opposed to each other in a perpendicular direction with respect to the longitudinal direction of the flow pipe (440), and formed so that the charged biological particles and the charged non-biological particles can be separately discharged;

the flow pipe (440) having one end on which the compressed air inlet (410) and the particle inlet (420) are formed and the other end on which the first outlet (431) and the second outlet (432) are formed and a flow path (441) formed therein to allow the biological particles and the non-biological particles to flow therealong; and a first charged electrode plate (451) and a second charged electrode plate (452) disposed on the side periphery of the flow pipe (440) in such a manner as to be opposed to each other and charged to different polarities from each other.

2. The apparatus according to claim 1, wherein the impactor (200) comprises:

an introduction channel (210) adapted to receive the biological particles and non-biological particles from the outside;

an auxiliary flow channel (230) disposed in the same direction as the flow direction of the particles introduced into the introduction channel (210); and one or more main flow channels (220) disposed in a vertical direction with respect to the flow direction of the particles introduced into the introduction channel (210).

3. The apparatus according to claim 1, wherein the charger (300) is formed of a charger using corona discharge.

4. The apparatus according to claim 1, wherein the charger (300) comprises:

a housing (310) having an introduction portion (311) adapted to introduce the biological particles and non-biological particles supplied from the impactor (200) thereinto and a discharge portion (312) adapted to discharge the charged biological particles and non-biological particles therefrom;

a charge electrode (320) disposed inside the housing (310) in such a manner as to allow the biological particles and non-biological particles flowing along the interior of the housing (310) to be charged by means of a predetermined voltage (340) applied thereto; and a ground electrode (330) disposed on the inner periphery of the housing (310) in such a manner as to be spaced apart from the charge electrode (320) by a predetermined distance, while having a grounded structure.

5. The apparatus according to claim 1, wherein the separator (400) further comprises a protrusion (460) formed between the first outlet (431) and the second outlet (432) in such a manner as to protrude inward from the flow pipe (440) by a predetermined length.

6. An apparatus (600') for in real time detecting biological particles and non-biological particles in the atmosphere, the apparatus (600') comprising:

a first impactor (201) adapted to sort the biological particles and non-biological particles supplied from the outside to discharge the biological particles and non-biological particles having diameters larger than a first particle diameter to the outside and to supply the biological particles and non-biological particles having diameters smaller than the first particle diameter to a second impactor (202);

the second impactor (202) adapted to sort the biological particles and non-biological particles supplied from the first impactor (201) to supply the biological particles and non-biological particles having diameters larger than a second particle diameter to a first charger (301) and to supply the biological particles and non-biological particles having diameters smaller than the second particle diameter to a third impactor (203);

the third impactor (203) adapted to sort the biological particles and non-biological particles supplied from the second impactor (202) to, supply the biological particles and non-biological particles having diameters larger than a third particle diameter to a second charger (302) and to supply the biological particles and non-biological particles having diameters smaller than the second particle diameter to a third charger (303);

the first charger (301) adapted to charge the biological particles and non-biological particles sorted by means of the second impactor (202) to specific charge (positive or negative charge);

the second charger (302) and the third charger (303) adapted to charge the biological particles and non-biological particles sorted by means of the third impactor (203) to specific charge (positive or negative charge);

a first separator (401) adapted to introduce the biological particles and non-biological particles charged by the first charger (301) thereinto and to sort the biological particles and non-biological particles charged to different charge quantities from each other by using predetermined air flow and electric force;

a second separator (402) adapted to introduce the biological particles and non-biological particles charged by the second charger (302) thereinto and to sort the biological particles and non-biological particles charged to different charge quantities from each other by using predetermined air flow and electric force;

a third separator (403) adapted to introduce the biological particles and non-biological particles charged by the third charger (303) thereinto and to sort the biological particles and non-biological particles charged to different charge quantities from each other by using predetermined air flow and electric force; and first, second and third particle measurement sensors (501, 502 and 503) mounted on outlets each discharging the biological particles and non-biological particles sorted through the first separator (401), the second separator (402) and the third separator (403) therefrom so as to measure the concentrations of the particles discharged from the outlets, wherein each of the first separator (401), the second separator (402) and the third separator (403) comprises:

a compressed air inlet (410) formed on one end of a flow pipe (440) to introduce the compressed air supplied from the compressed air supplier (110) thereinto;

a particle inlet (420) formed on one end of the flow pipe (440) to introduce the charged biological particles and non-biological particles thereinto;

a first outlet (431) and the second outlet (432) formed on the other end of the flow pipe (440) in such a manner as to be opposed to each other in a perpendicular direction with respect to the longitudinal direction of the flow pipe (440), and formed so that the charged biological particles and the charged non-biological particles can be separately discharged;

the flow pipe (440) having one end on which the compressed air inlet (410) and the particle inlet (420) are formed and the other end on which the first outlet (431) and the second outlet (432) are formed and a flow path (441) formed therein to allow the biological particles and the non-biological particles to flow therealong; and a first charged electrode plate (451) and a second charged electrode plate (452) disposed on the side periphery of the flow pipe (440) in, such a manner as to be opposed to each other and charged to different polarities from each, other.

7. The apparatus according to claim 6, wherein each of the first impactor (201), the second impactor (202) and the third impactor (203) comprises:

an introduction channel (210) adapted to receive the biological particles and non-biological particles from the outside;

an auxiliary flow channel (230) disposed in the same direction as the flow direction of the particles introduced into the introduction channel (210); and one or more main flow channels (220) disposed in a vertical direction with respect to the flow direction of the particles introduced into the introduction channel (210).

8. The apparatus according to claim 6, wherein each of the first charger (301), the second charger (302) and the third charger (303) is formed of a charger using corona discharge.

9. The apparatus according to claim 6, wherein each of the first charger (301), the second charger (302) and the third charger (303) comprises:

a housing (310) having an introduction portion (311) adapted to introduce the biological particles and non-biological particles supplied from the impactor (200) thereinto and a discharge portion (312) adapted to discharge the charged biological particles and non-biological particles therefrom;

a charge electrode (320) disposed inside the housing (310) in such a manner as to allow the biological particles and non-biological particles flowing along the interior of the housing (310) to be charged by means of, a predetermined voltage (340) applied thereto; and a ground electrode (330) disposed on the inner periphery of the housing (310) in such a manner as to be spaced apart from the charge electrode (320) by a predetermined distance, while having a grounded structure.

10. The apparatus according to claim 6, wherein each of the first separator (401), the second separator (402) and the third separator (403) further comprises a protrusion (460) formed between the first outlet (431) and the second outlet (432) in such a manner as to protrude inward from the flow pipe (440) by a predetermined length.

11. A method for detecting biological particles and non-biological particles using, an apparatus (600) according to claim 1, the method comprising the steps of:

absorbing the biological particles and non-biological particles suspended in the atmosphere, together with air, through the impactor (200);

sorting the biological particles and non-biological particles in the atmosphere absorbed from the outside by size by means of the impactor (200);

charging the biological particles and non-biological particles sorted by the impactor (200) to specific charge (positive or negative charge) through the charger (300);

charging the biological particles and non-biological particles charged by the charger (300) to different charge quantities and <sorting the biological particles and non-biological particles charged to the different charge quantities through the separator (400); and measuring the concentrations of the particles sorted by the separator (400) through the particle measurement sensor (500).

12. A system (700) for in real time detecting biological particles and non-biological particles suspended in the atmosphere, the system (700) comprising:
- an apparatus (600) according to claim 1;
- a controller (710) controlling the driving of the apparatus (600);
- a data calculator (720) connected to the particle measurement sensor (500) and adding up the concentrations of the particles detected by the particle measurement sensor (500) to calculate the result data; and
- a display screen (730) displaying the result data calculated from the data calculator (720).

13. The system according to claim 12, wherein the system (700) is formed of a portable integral type module.

* * * * *